US007458985B2

(12) United States Patent
Madda et al.

(10) Patent No.: US 7,458,985 B2

(45) Date of Patent: Dec. 2, 2008

(54) SPIRAL STENT ASSEMBLY

(76) Inventors: Frank Madda, 1585 N. Barrington Rd., Suite 601, Hoffman Estates, IL (US) 60194; James Schuler, 5544 S. County Line Rd., Hinsdale, IL (US) 60521

( * ) Notice: Subject to any disclaimer, the term of this patent is extended or adjusted under 35 U.S.C. 154(b) by 859 days.

(21) Appl. No.: 10/765,553

(22) Filed: Jan. 27, 2004

(65) Prior Publication Data

US 2005/0080481 A1 Apr. 14, 2005

Related U.S. Application Data

(60) Provisional application No. 60/459,850, filed on Apr. 2, 2003, provisional application No. 60/442,842, filed on Jan. 27, 2003.

(51) Int. Cl.
*A61F 2/06* (2006.01)

(52) U.S. Cl. .................................................... 623/1.15

(58) Field of Classification Search ................ 623/1.11, 623/1.15, 1.2; 606/191, 194, 195, 198
See application file for complete search history.

(56) References Cited

U.S. PATENT DOCUMENTS

| | | | | |
|---|---|---|---|---|
| 4,130,904 | A | 12/1978 | Whalen | |
| 4,503,569 | A | 3/1985 | Dotter | |
| 5,562,641 | A * | 10/1996 | Flomenblit et al. | 604/531 |
| 2004/0093075 | A1 * | 5/2004 | Kuehne | 623/1.15 |

* cited by examiner

*Primary Examiner*—Kevin T Truong
(74) *Attorney, Agent, or Firm*—Marshall, Gerstein & Borun LLP

(57) ABSTRACT

A stent assembly includes a spiral shaped elongate member having a first end and a second end. The elongate member includes a plurality of loops spaced apart from each other. A first contact is attached to and near the first end of the elongate member, and a second contact is attached to and near the second end of the elongate member. The first and second contacts are coupled to a power generator, thereby allowing for a current to be passed from the first contact to the second contact.

12 Claims, 20 Drawing Sheets

22
64
10
40

89
10
14a
110
110
112
100
90a
96
90a
102
102
90a
23
23
98
102
14b 102
90a
10

SPIRAL STENT ASSEMBLY

RELATED APPLICATION DATA

The present application is a non-provisional application based on, and claiming the priority benefit of, U.S. Provisional Application Ser. No. 60/442,842, which was filed on Jan. 27, 2003, and U.S. Provisional Application Ser. No. 60/459,850, which was filed on Apr. 2, 2003, which are expressly incorporated by reference herein.

TECHNICAL FIELD

The present invention relates generally to vascular stents and, more particularly, to a spiral shaped stent.

BACKGROUND

Prosthetic devices for use within bodily orifices are known in the art and have been used for many years. More recently, however, the use of spiral shaped prosthetic devices and portion thereof, have also become known in the art. For example, U.S. Pat. No. 4,130,904 discloses a prosthetic conduit having two porous concentrically associated tubes with a helical spring enclosed therebetween. The spring enables the conduit to resist collapse under a wide variety of stress forces, and the convolutions in the tube walls provide flexibility without kinking.

U.S. Pat. No. 4,503,569 discloses a transluminally placed endovascular graft prosthesis including a helically wound coil having a generally tubular shape that is made of a heat sensitive shape memory material. After placement within a body orifice and upon heating of the prosthesis, the prosthesis expands so as to become firmly anchored within the wall of the orifice.

This and other prosthetic devices, however, also have inherent limitations. For example, this prosthetic device is limited to being reduced in the size or shrunk is only one manner, i.e. reducing the diameter of the prosthetic device. Similarly, it is difficult for this and other prosthetic devices to be tested for integrity and/or failure. For example, to determine the condition of currently available prosthetic devices, either an X-ray needs to be taken, which may not even provide all the necessary information, such as cracks, wear, etc., and/or an invasive procedure needs to be conducted.

SUMMARY

In accordance with one aspect of the disclosure, a stent assembly having a spiral shaped elongate member, and a first and second contact is disclosed. The elongate member includes a plurality of spiraling loops extending between a first end and a second end of the elongate member, that are being spaceable so as not to touch each other. The first contact is attached adjacent the first end of the elongate member, and the second contact is attached adjacent the second end of the elongate member. The first and second contacts are coupled to a power generator that is arranged to allow a current to be passed from the first contact to the second contact.

In accordance with another aspect of the disclosure, a stent assembly, having a spiral shaped elongate member and an intermediate support, is disclosed. The spiral shaped elongate member includes a first end, a second end, and a plurality of loops, and the intermediate support zig-zags back and forth between each loop and the next adjacent loop.

In accordance with another aspect of the disclosure, a method of inserting a stent assembly, is disclosed. The method includes providing a spiral shaped elongate member having a plurality of loops that are spaced so as not to touch each other in an expanded position, and moving a first portion of the spiral shaped elongate member in a first direction and moving a second portion of the spiral shaped elongate member, opposite the first portion, in a second direction that is opposite the first direction. The method further includes abutting a first of the plurality of loops against a second of the plurality of loops, thereby placing the spiral shaped body in a reduced position.

In accordance with another aspect of the disclosure, a method of testing a stent assembly, is disclosed. The method includes contacting a first end of a spiral shaped elongate member with a power generator, and placing a current between the first end and a second end of the spiral shaped elongate member. The method further includes measuring a resistance between the first end and the second end of the spiral shaped elongate member.

In accordance with another aspect of the disclosure, a stent assembly having a spiral shaped elongate member, is disclosed. The spiral shaped elongate member includes a first end, a second end, and a plurality of loops. A first set of loops, of the plurality of loops, is disposed between the first end and the second end of the elongate member, and a second set of loops, of the plurality of loops, adjacent the first set of loops, is disposed between the first end and the second end of the elongate member. The spacing between the loops of the first set of loops is greater than a spacing between the loops of the second set of loops.

In accordance with another aspect of the disclosure, a stent assembly includes a spiral shaped elongate member, a fluid distribution member, and a fluid connection member. The spiral shaped elongate member has an inner surface that defines a lumen for the entry and exit of blood and an outer surface. The fluid distribution member has an inlet and at least one outlet, and is at least partially disposed over the spiral shaped elongate member. The fluid connection member has an inlet that is fluidly connected to a reservoir, and an outlet that is fluidly connected to the inlet of the fluid distribution member.

In accordance with another aspect of the disclosure, a stent assembly includes a spiral shaped elongate member having at least one set of hinges. The spiral shaped elongate member includes a first end, a second end, and a plurality of loops. The at least one set of hinges is disposed between the first and second end of the spiral shaped elongate member, and is axially aligned along a length of the spiral shaped elongate member.

Figure 1:
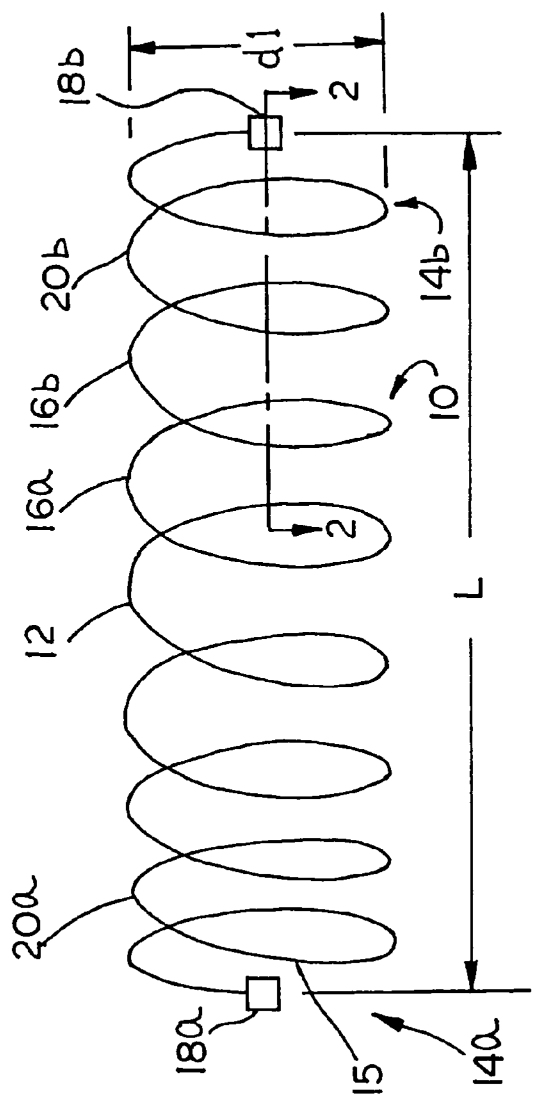
FIG. 1 is a side view of one embodiment of a spiral stent in an expanded position.

While the method and device described herein are susceptible to various modifications and alternative constructions, certain illustrative embodiments thereof have been shown in the drawings and will be described below in detail. It should be understood, however, that there is no intention to limit the invention to the specific forms disclosed, but on the contrary, the intention is to cover all modifications, alternative constructions, and equivalents falling within the spirit and scope of the invention as defined by the appended claims.

DETAILED DESCRIPTION

Figure 2:
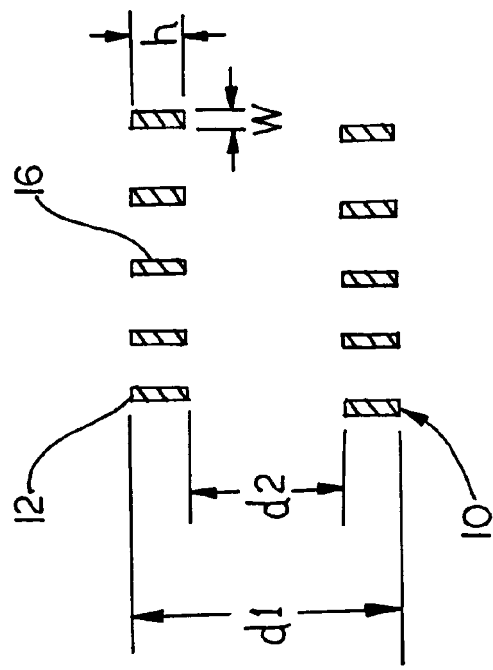
FIG. 2 is a cross-sectional view of the spiral stent taken along lines 2-2 of FIG. 1.

Referring now to the drawings, and with specific reference to FIG. 1, a spiral stent constructed in accordance with the teachings of the disclosure is generally depicted by reference numeral 10. In one embodiment, the stent 10 is a helically wound, continuous elongate member 12, and in this exemplary embodiment, is a strip 12. The strip 12, as seen in FIG. 2, includes an outer diameter D1, an inner diameter D2, and a flexible longitudinal length L. It will be understood that the diameters may change in response to lengthening the stent 10 in the longitudinal direction. The stent 10 includes a pair of ends 14*a* and 14*b* (FIG. 1), and defines an interior lumen 15 having a diameter generally the same as the inner diameter D2. The stent 10 is readily resilient or elastic in the direction of its longitudinal length L, and may be comparatively stiff in the direction transverse to its length L. The strip 12 may be wound into several loops, for example 16*a*, 16*b*, . . . , 16*n*, in which none of the loops are in contact with each other when the stent 10 is an expanded position as shown in FIG. 1. The strip 12 may be constructed of stainless steel or any other conventional material for the manufacture of stents, or it may be constructed from a material coated with a polymer. Other materials may prove suitable as well.

At first and second ends 14*a*, 14*b* of the stent 10 are free ends 18*a* and 18*b*, respectively, of the strip 12. The free ends 18*a* and 18*b* of the strip 12 may be attached to their next adjacent loops 20*a* and 20*b*, respectively. The free ends 18*a* and 18*b* may, however, be attached to their adjacent loops 20*a* and 20*b* by any means known, or that become known, in the art such as welding, bonding, crimping, etc. Furthermore, it is possible that the free ends 18*a* and 18*b* are not attached to the next loops 20*a* and 20*b*, but that the free ends 18*a* and 18*b* are unattached to and move independently of their adjacent loops 20*a* and 20*b*.

As shown in FIG. 2, the strip 12, and more specifically, the loops 16 of the stent 10 have, in this exemplary embodiment, a width W and a height H. To increase strength in the radial direction of the stent 10, the height H may be greater than the width W. However, in some conditions, it may be more important to maximize the interior diameter D2 of the stent 10. In this case, the height H may be decreased to the point that the width W is greater than the height H. The cross-section of the strip 12 may further be in the shape of a circle, ellipse, or any other shape that could be helpful for the patient.

Figure 3:
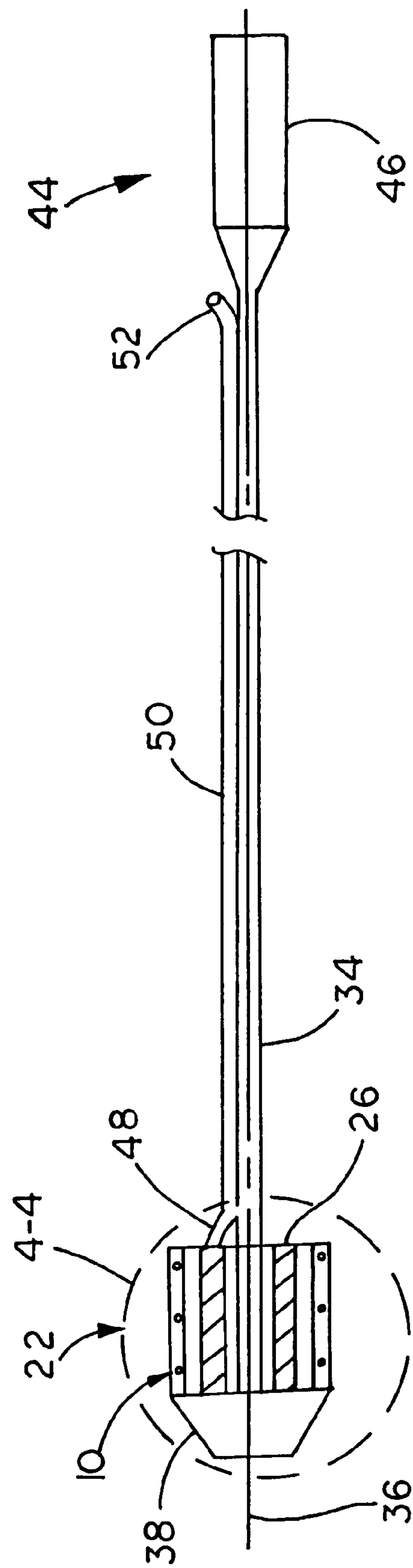
FIG. 3 is a side view, with parts in cross-section, of a stent delivery device.

A stent delivery device 22, as seen in FIG. 3, includes balloon 26, a catheter 34, a user end 44, and a handle 46. The user end 44 includes the handle 46 which is grasped and manipulated by the user. The balloon 26 is fluidly connected to an outlet 48 of a balloon tube 50. The balloon tube 50 has an inlet 52 which can be attached to a conventional valve (not shown). The user controls the size of the balloon 26 by inserting and retracting fluid into and out of the balloon 26 through the balloon tube 50, as is well known in the art.

Figure 4:
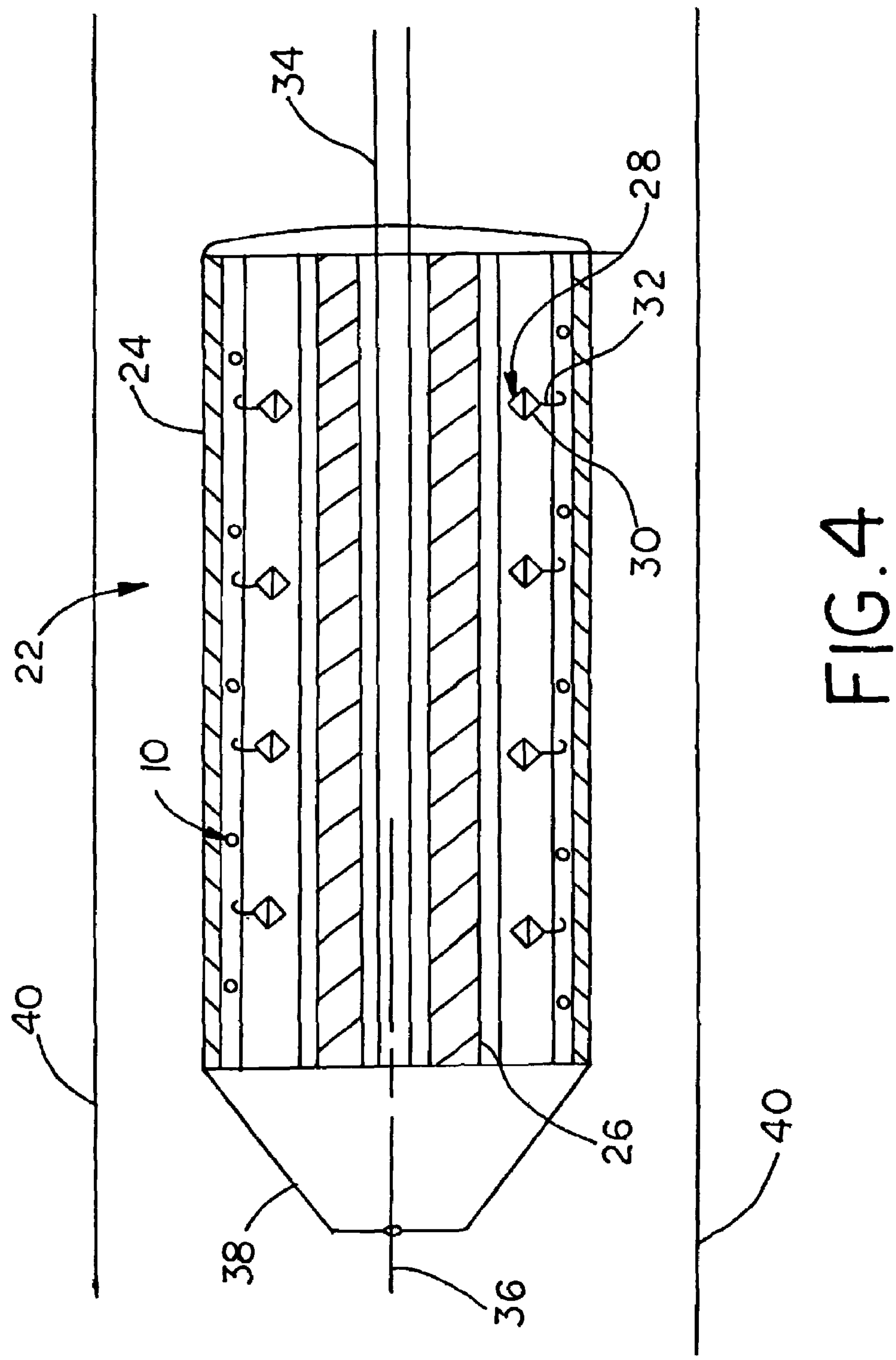
FIG. 4 is a detailed view of section 4-4 of FIG. 3, having a deflated balloon.

The stent delivery device 22, and more specifically, the balloon 26, as seen in FIG. 4, may be deflated prior and during the entry of the stent delivery device 22 into, for example, a vascular system, and may include a vascular graft 24. The graft 24 can be manufactured of Gore-Tex® or another similar flexible material of the type commonly employed in the art. The stent 10 and the graft 24 are shown surrounding an unexpanded balloon 26. Disposed between the stent 10 and the balloon 26 is a plurality of grippers 28 having a collapsing element 30 and a hook 32, with each gripper 28 being disposed between adjacent loops 16*a*, 16*b*, . . . 16*n* of the stent 10. Within the balloon 26 may be the catheter 34, and within the catheter 34 may be a guide wire 36. On the end of the catheter 34 is a distal tip 38. As shown in FIG. 4, the delivery device 22 has been positioned inside a blood vessel 40 targeted for treatment.

Figure 5:
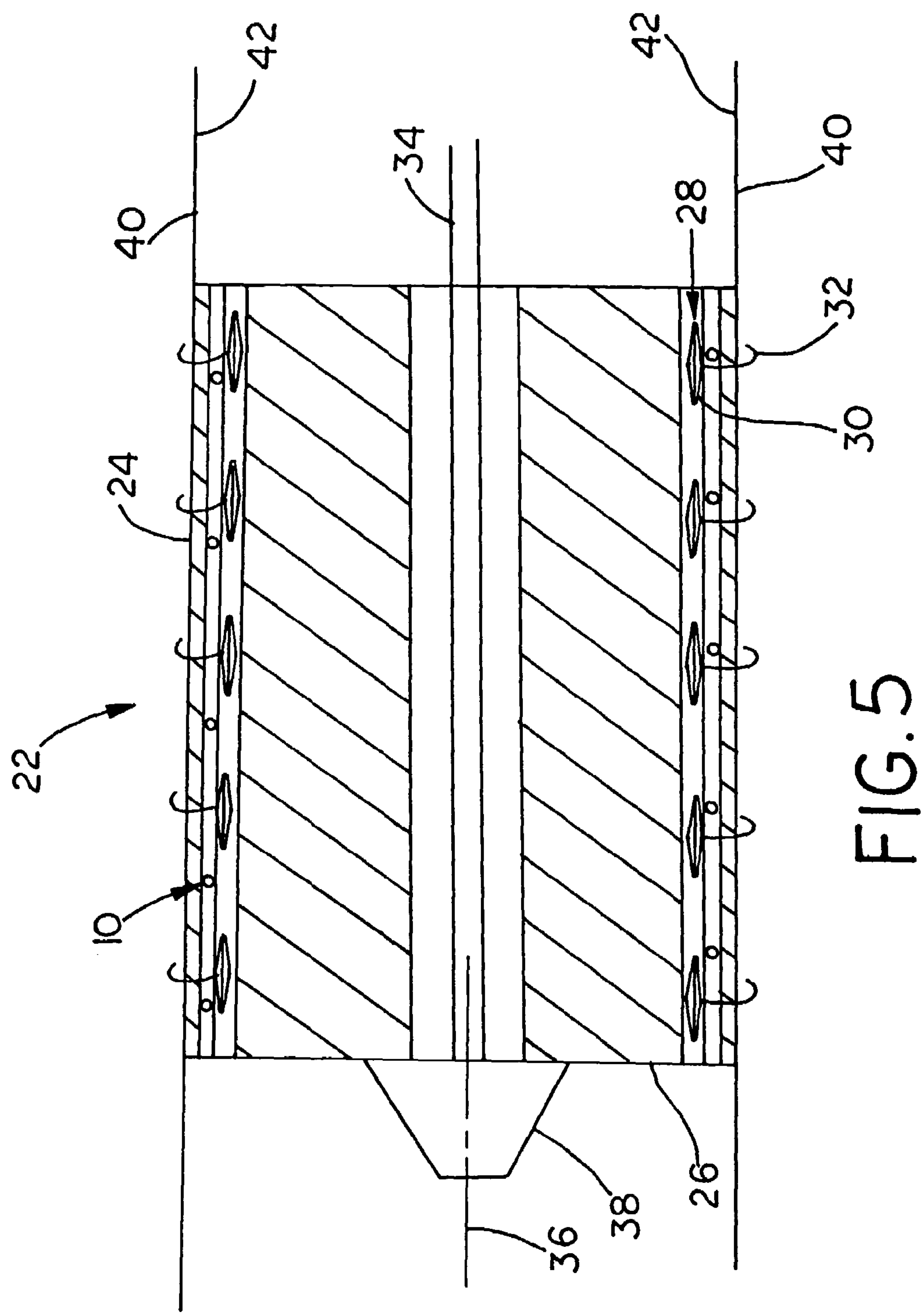
FIG. 5 a detailed view of section 4-4 of FIG. 3, having an inflated balloon.
Figure 6:
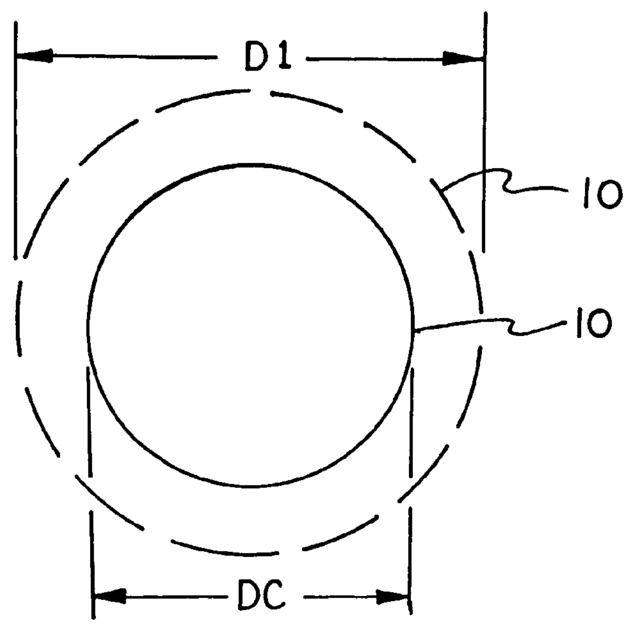
FIG. 6 is a front view of the spiral stent of FIG. 1 in a coiled position.

The stent delivery device 22, and more specifically, the balloon 26 may be inflated once the stent delivery device 22 has reached the intended location. More specifically, as seen in FIG. 5, once the balloon 26 is being inflated and/or is inflated, the collapsing elements 30 of the grippers 28 may be flattened, in turn pushing the hooks 32 outwardly and through the graft 24 and into contact with inside walls 42 of the blood vessel 40. An outer surface of the graft 24 is now suitably secured to the blood vessel 40. The hooks 32 likewise have been pressed radially outward into the blood vessel 40, thereby locking the stent 10 and the graft 24 at the desired location within the blood vessel 40. This process may be one of many possible processes for placing the spiral stent 10 in the vessel 40. Before the balloon 26 is inflated, the stent 10 may be reduced in size to fit into the vessel 40, by coiling the stent 10 into a tighter spiral, thus decreasing the diameter D1 to diameter DC, as seen in FIG. 6. By expanding the balloon 26 within the stent 10, the stent 10 uncoils, and the diameter D1 thereby increases. Other possible methods of collapsing and expanding the stent 10 will be discussed later.

Figure 7:
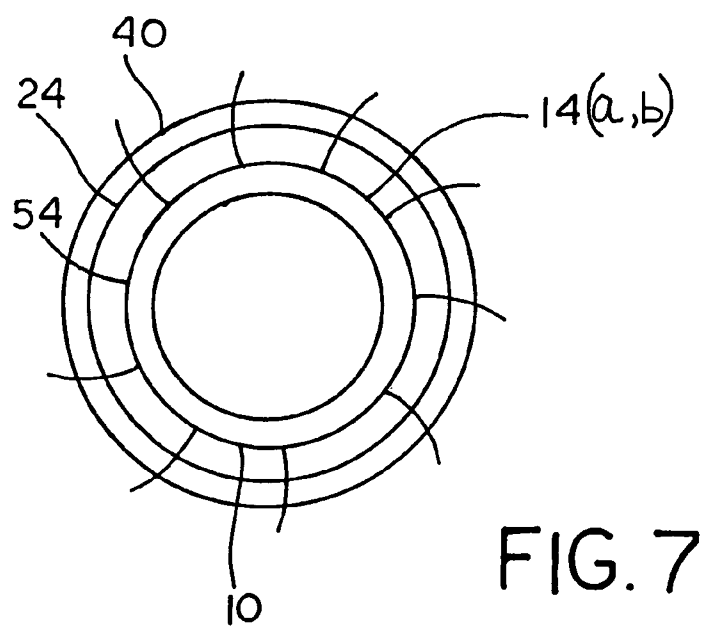
FIG. 7 is an end view of the spiral stent of FIG. 1 and a graft.

Additionally and/or alternatively to the hooks 32, the stent 10, and more specifically, the ends 14*a* and 14*b* of the stent 10, may further include a plurality of landing hooks 54, as seen in FIG. 7. The hooks 54, in this exemplary embodiment, work in much the same manner as the hooks 32 of the previous example in that when the stent 10 is expanded, the hooks 54 push into the blood vessel wall 40, and lock the stent 10 into place. However, the hooks 54 may be disposed distal and proximal to the ends of the graft 24, and thus, when the stent 10 is expanded, the hooks 54 do not puncture the graft 24. Alternatively, the stent 10 may have additional hooks 54 disposed at suitable intervals along its length L.

Figure 8:
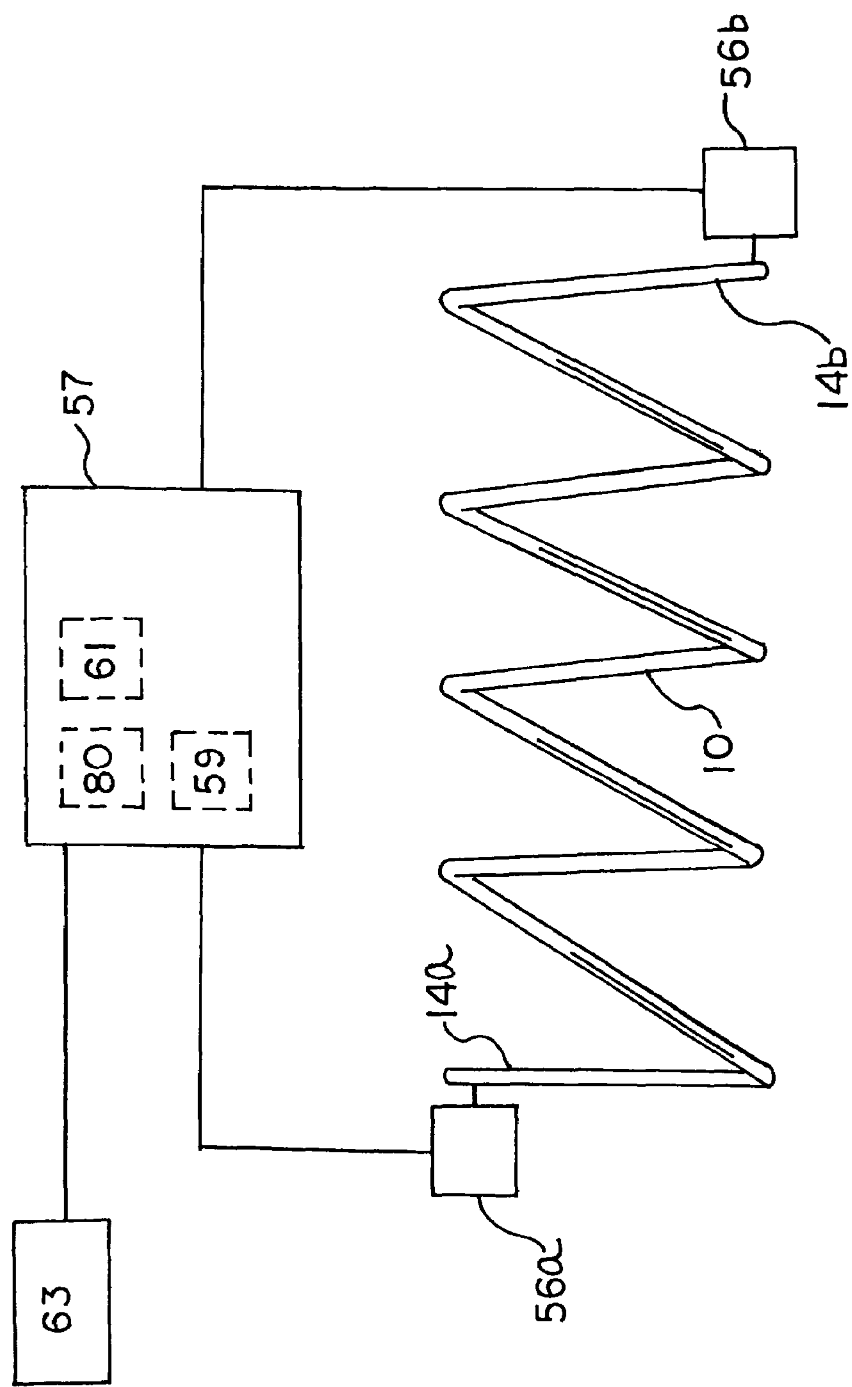
FIG. 8 is a side view of the spiral stent of FIG. 1, with contacts adjacent ends of the stent.

One or more electrical contacts 56, as seen in FIG. 8, may be disposed on the stent 10, and more specifically, a first electrical contact 56*a* may be disposed adjacent the end 14*a*, and a second electrical contact 56*b* may be disposed adjacent the end 14*b*. By placing a voltage or other type of current across the electrical contacts 56*a* and 56*b*, it may be quickly discernable that the stent 10 has remained in one continuous piece if a current flows between the contacts 56*a* and 56*b*. On the other hand, if the stent 10 has failed, for example has broken into two or more pieces, no current will flow. Furthermore, if the stent 10 degrades over time, such as a crack forming in the stent 10, material of the stent 10 wearing off, and/or the stent 10 corrodes, the stent 10 will show an increase or other change of resistance between the contacts 56*a* and 56*b*. Thus, by placing a current across the contacts 56*a* and 56*b* of the stent 10, it may also be determined that the stent 10 is degrading and/or is in danger of failing before the actual failure occurs.

The voltage and/or current, across the contacts 56*a* and 56*b* may be produced by an internal or external power source 80. For example, a subcutaneous pack 57, including a battery 80 may be located near and be electrically coupled to the stent 10. A current and/or voltage may then be passed between the contacts 56*a* and 56*b*, which may then be measured using measuring device 59, such as a voltmeter, or the like. The relevant voltage/current information may then be communicated from the subcutaneous pack 57 via an internal communications device 61 to an external communications device 63. Other forms of external and internal power may be used to effectuate the above process, some of which will be discussed in more detail below.

Figure 9:
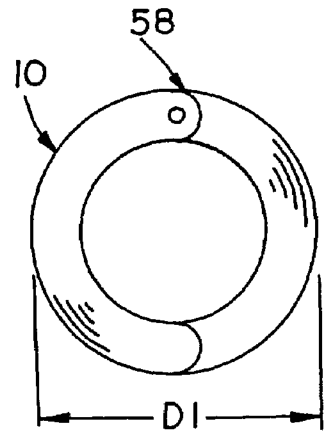
FIG. 9 is a front view of an expanded spiral stent including a single axis of hinges.
Figure 10:
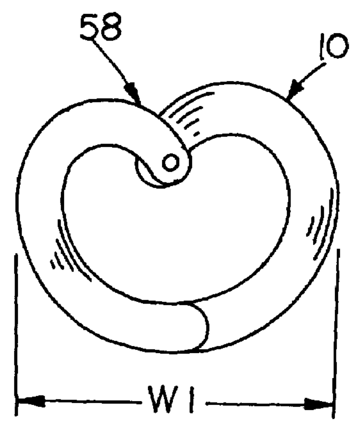
FIG. 10 is a similar view to FIG. 9, with the spiral stent in a reduced position.

In another exemplary embodiment, as seen in FIG. 9, the stent 10 may include a first set of hinged portions 58. More specifically, the stent 10 may have the first set of hinged portions 58 located at substantially the same location on each successive loop 16*a*, 16*b*, etc. As such, the stent 10 may hinged along its longitudinal length L and, therefore, able to collapse along the longitudinal length L, such that the expanded diameter D1 can be lessened to a reduced diameter W1 (FIG. 10). When the stent 10 is expanded to diameter D1 from the collapsed state, the stent 10 can be maintained in the expanded position in any of several ways known or hereafter known in the art, including interlocking latches, etc. Alternatively, the natural resilience of the balance of the loops 16 may be sufficient to maintain the stent 10 in the expanded state. Furthermore, the first set of hinged portions 58 may be replaced with other structure and method known to resiliently collapse a circle, such as for example, a line of weakness in the stent 10.

Figure 11:
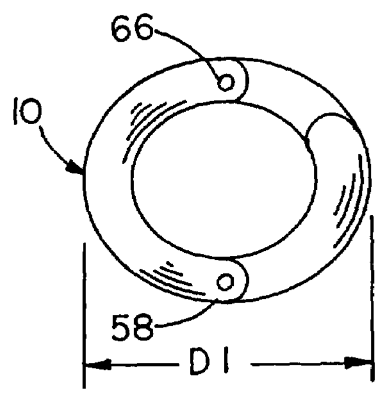
FIG. 11 is a front view of an expanded spiral stent including a first and a second axis of hinges.
Figure 12:
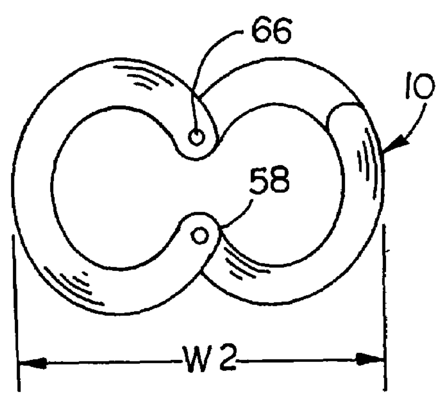
FIG. 12 is a similar view to FIG. 11, with the spiral stent in a reduced position.

Alternatively, the stent 10 may include a plurality of hinge sets and may, as in this exemplary embodiment, include a first and second hinge set 58, 66. As seen in FIG. 11, the number of hinge sets may be increased to achieve an even greater difference in the size of the stent 10 from the expanded position to the reduced/collapsed position. As can be seen by comparing FIGS. 11 and 12, expanded diameter D1 is greater that collapsed size W2. Also, the collapsed size W1 of FIG. 10 is greater than the collapsed size W2 of FIG. 12.

Figure 13:
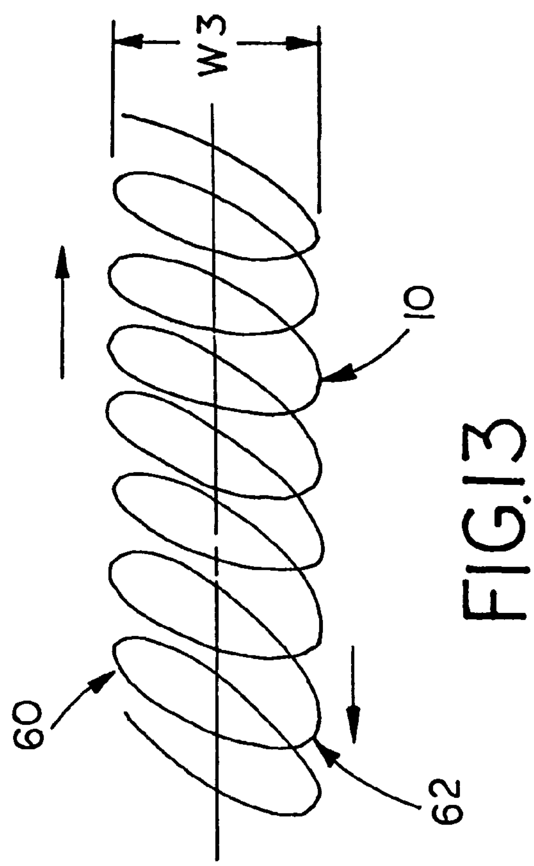
FIG. 13 is a side view of the spiral stent of FIG. 1 in a reduced position.
Figure 14:
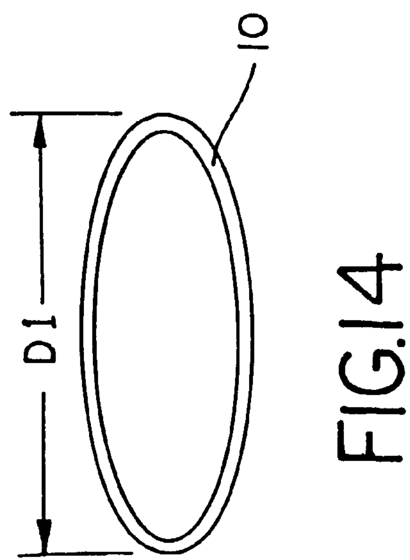
FIG. 14 is a rear view of the spiral stent of FIG. 13.

The stent 10 may, as was eluded to previously, be collapsed in additional ways prior to placement within the vasculature structure of a patient. For example, an upper portion 60 of the stent 10 and a lower portion 62 of the stent 10 may be moved in opposite directions, such that the stent 10 effectively flattens out, as seen in FIG. 13. While the width of the stent 10 still has a width equal to diameter D1, as seen in FIG. 14, the height of the stent is decreased to a flattened height W3 (FIG. 13). In such a configuration, the stent 10 may be inserted through a suitably sized slit in the wall of the vessel. The stent 10 may, however, have a reduced diameter DC, W1, or W2 prior to being reduced or collapse as described above. As such the stent 10 would have a width approximately equal to diameters DC, W1, or W2, and a height approximately equal to W3.

Figure 15:
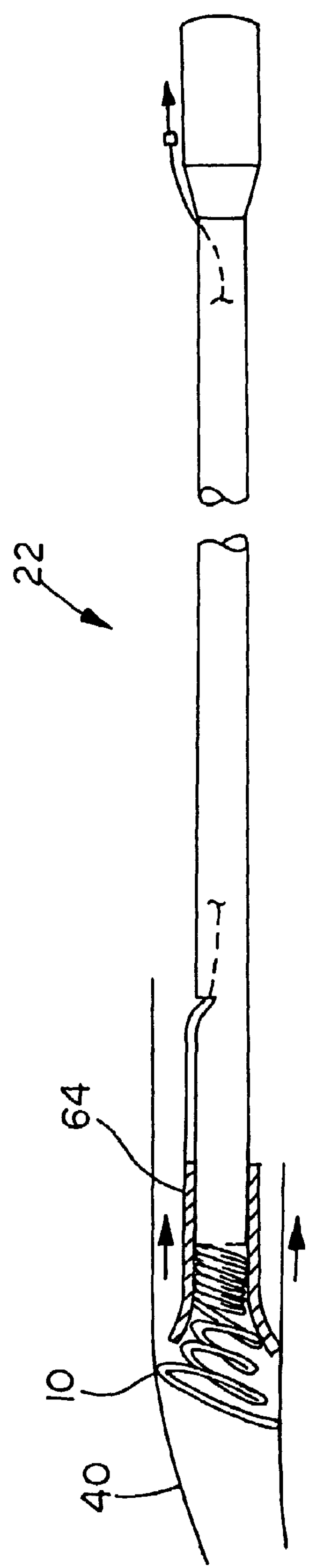
FIG. 15 is a side view of a stent delivery device, in partial cross-section, for the stent of FIG. 1, utilizing a sheath.

A further method, as shown in FIG. 15, of decreasing the cross-section area of the stent 10, is to employ a sheath 64 such that stent 10 may be a self-expanding stent. In this exemplary method, the sheath 64 is disposed over the stent 10 to collapse the stent 10, and/or is disposed over the stent 10 once the stent 10 has already been collapsed. The stent 10 is then located at the proper area within the patient's vasculature 40 and the sheath 64 is removed. The stent 10 may then expand within the blood vessel 40 to provide the necessary support.

When assembled in accordance with the teachings of the disclosure, the stent 10 may include one or more of the following characteristics. Under the harmonic pulsing of the heart beat and the rushing of the blood, a more conventional stent may flex and each piece must move independently to accommodate this flexing. The individual pieces in a conventional stent may experience metal on metal wear which induces wear hardening, and ultimately, some portion of the stent structure may fail. When a typical stent fails, it may be difficult to predict how and where an individual metal piece may react, and it is further very difficult to detect when a failure has occurred. The disclosed method of using an electrical voltage across the stent 10 may be difficult or impossible with a conventional stent, since a conventional stent has a web of metal strips, and will generally still be able to carry a current if one or more of the pieces breaks.

Figure 16:
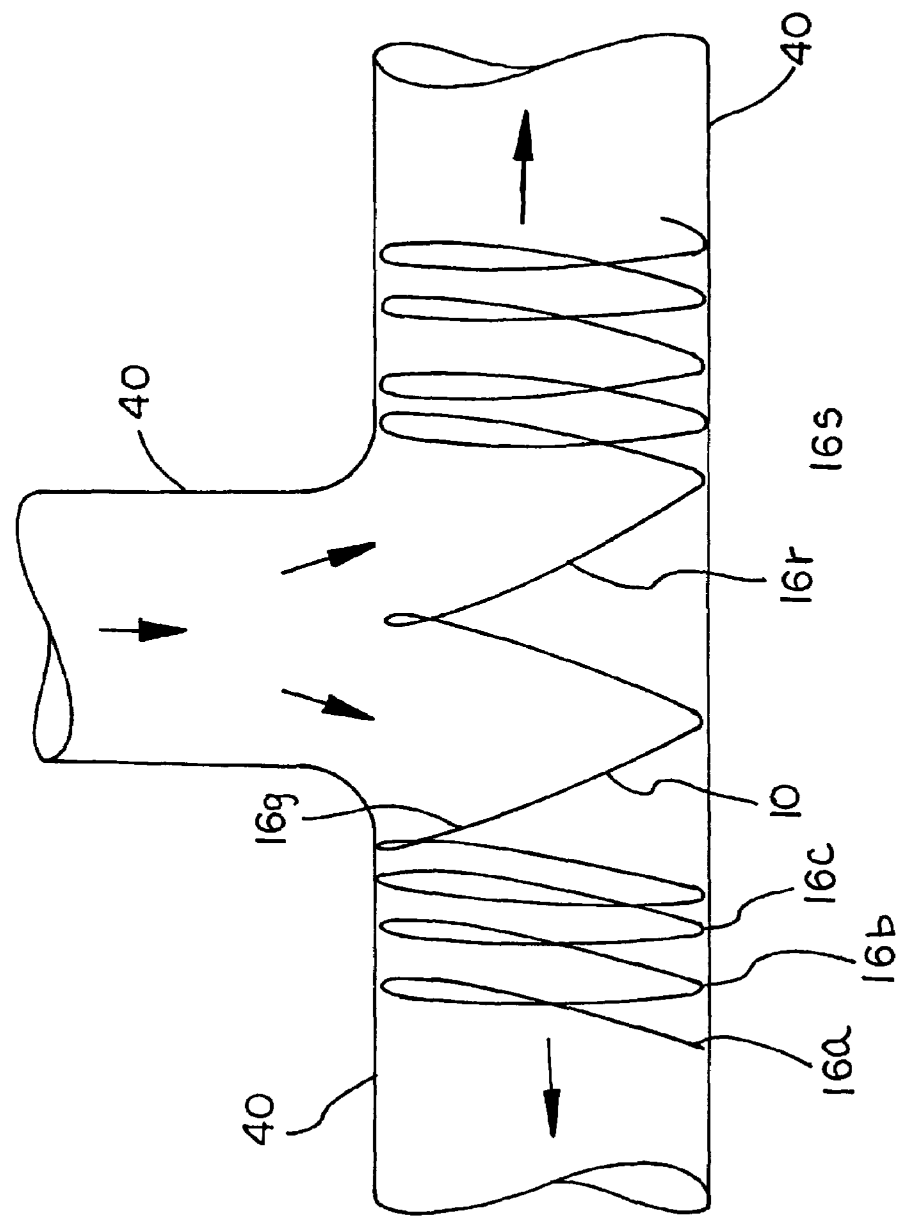
FIG. 16 is a side view of the spiral stent of FIG. 1 situated at a vascular junction.

The disclosed stent 10 may reduce or eliminate the wear hardening associated with conventional stents. The single wire design with no metal to metal contact and the spiral (slinky) nature allows movement of a harmonic nature (FIG. 1) which does not cause wear hardening and stress fractures and there is no metal to metal contact at all with connecting longitudinal wire as present stents contain. This characteristic may extend the serviceable life of the stent 10. Also, a broken piece of the stent 10 does not pierce the inner wall 42 of the vessel 40 due to the stent's 10 orientation and because it is curved similar to the vessel 40. Furthermore, the detection of a failure is simple if the electrical contacts 56 are included as previously described. The shape of the stent 10, that being a helical winding, is naturally diametrically stronger than a standard stent, and thus the strip 12 can be made thinner and less intrusive and still maintain the lumen 15. Due to the flexible nature of a helical winding, the disclosed stent 10 can easily be used in a corner without the loss of the lumen 15. Finally, the helical stent 10 as described may be placed so as to have different spacing between the loops 16*a*, 16*b*, . . . , 16*n*, as seen in FIG. 16. For example, if strength is necessary at a particular location, the spacing between the loops 16*a*, 16*b*, and 16*c* may be very small or denser. At another location, loops 16*q*, 16*r*, and 16*s* may be spaced far apart to accommodate the blood flow from an arterial branch that is attached to the blood vessel within the area supported by the stent 10. Thus, a hole need not be cut into the stent 10 to accommodate branch blood flow.

In one exemplary method of use, referring again to FIG. 3, the guide wire 36 may be percutaneously inserted into a patient and fed by a doctor in a known manner through the patient's vasculature structure until it reaches past the area targeted for treatment. The stent delivery device 22 is then fed with the stent 10 being in a collapsed state over the guide wire 26 and into the patient's vasculature system following along the guide wire 26 until the delivery device 22 reaches the targeted area. The stent 10 can be collapsed in any known method. Once the delivery device 22 is located at the targeted area, the surgeon inflates the balloon 26 by forcing saline or a similar liquid through the tube 50 and the outlet 48. This forces the stent 10 to expand against the interior wall 42 of the blood vessel 40. In one exemplary embodiment, the hooks 32 may then lock the stent 10 and graft 24 in place. Once the stent 10 and graft 24 are in the proper location, the balloon 26 may be deflated by withdrawing the saline. Because the stent 10 and the graft 24 have expanded to a larger diameter than the distal tip 38, the stent delivery device 22 can then simply be retracted out of the patient's vasculature.

Figure 17:
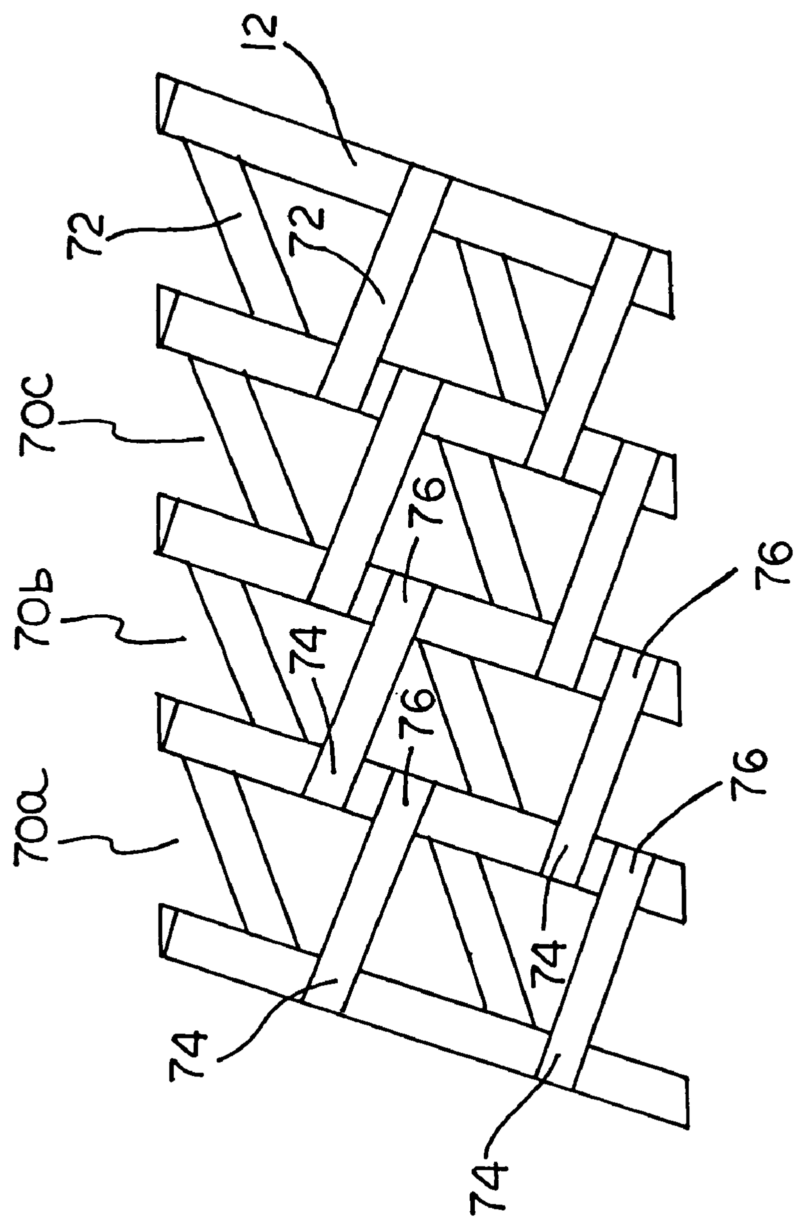
FIG. 17 is a side view of another embodiment of a spiral stent in an expanded position.
Figure 18:
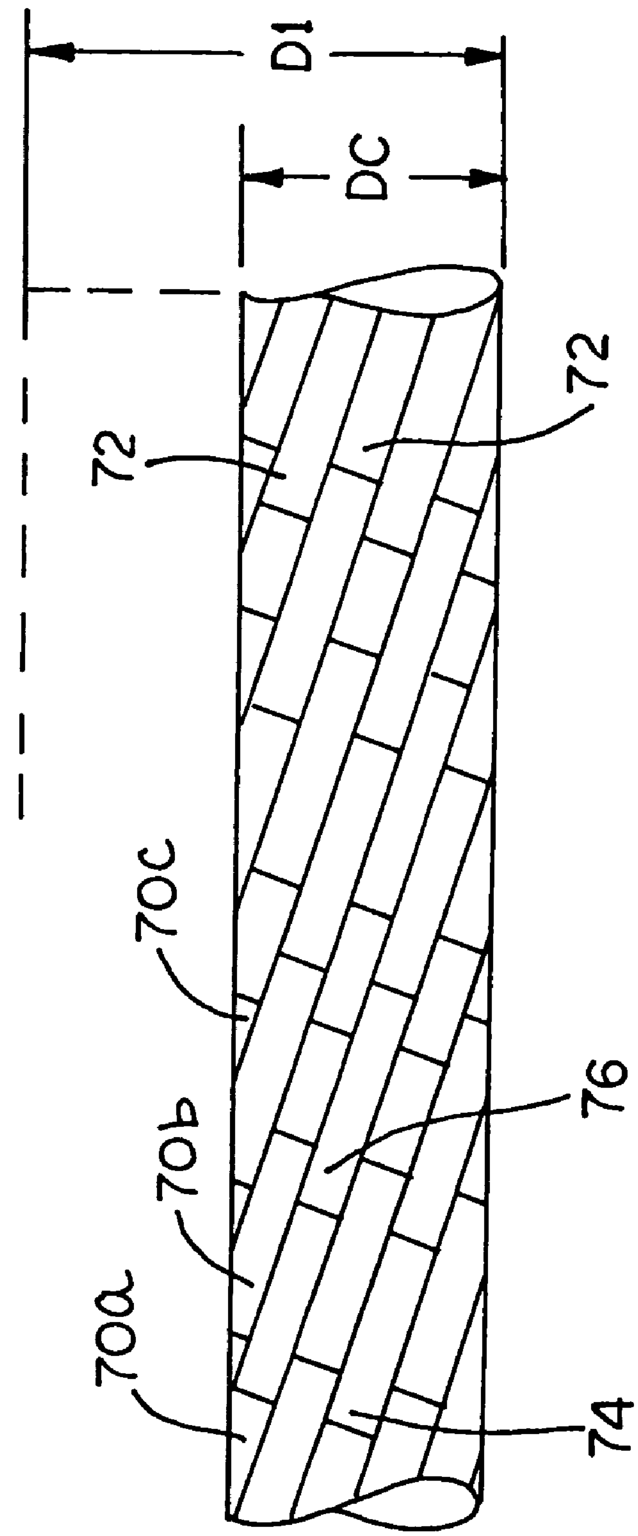
FIG. 18 is a side view of the spiral stent of FIG. 17 in a reduced position.

Additionally and/or alternatively to the above described exemplary embodiments, the stent 10, as seen in FIG. 17, may further include one or more intermediate sections 70*a*, 70*b*, 70*c*, . . . 70*n*, and may include one less intermediate section 70 than there are number of loops 16. Alternatively, the intermediate sections 70 may be constructed from a second elongate member or strip 72, thereby creating a pattern corresponding to and along the first strip 12. The intermediate sections 70 may be constructed from the same or similar conducive material as the strip 12 of the stent 10, but may also be constructed from a non-conductive material. More specifically, as seen in FIG. 17, the intermediate sections 70, and in this exemplary embodiment the first intermediate section 70*a*, includes a first section 74 adapted to engage the first loop 16*a* and a second section 76 adapted to engage the second loop 16*b*. As such, the second intermediate section 70*b* may include the first section 74 adapted to engage the second loop 16*b* and the second section 76 adapted to engage the third loop 16*c*, etc. In this exemplary embodiment, the intermediate sections 70 are pleated in shallow or deep accordion-like pleats, and may be as tightly or loosely wound as desired. The tighter or closer the spiral is, the greater the amount of wall support. However, changing the tightness of the spiral may have an effect on the compression of the stent 10. In one exemplary embodiment, the spacing allows overlapping of the pure spiral form by the pleats of the pattern. For example, as seen in FIG. 18, the intermediate section 70*a*-70*n* may cradle or correspond to each other, such that as the diameter D1 of the stent 10 is reduced and/or tightened to the diameter DC. The intermediate sections 70 may collapse onto each other, thereby bringing the strip 72 closer to each other while keeping the first and second sections 74, 76 of the intermediate portions 70 apart.

Figure 19:
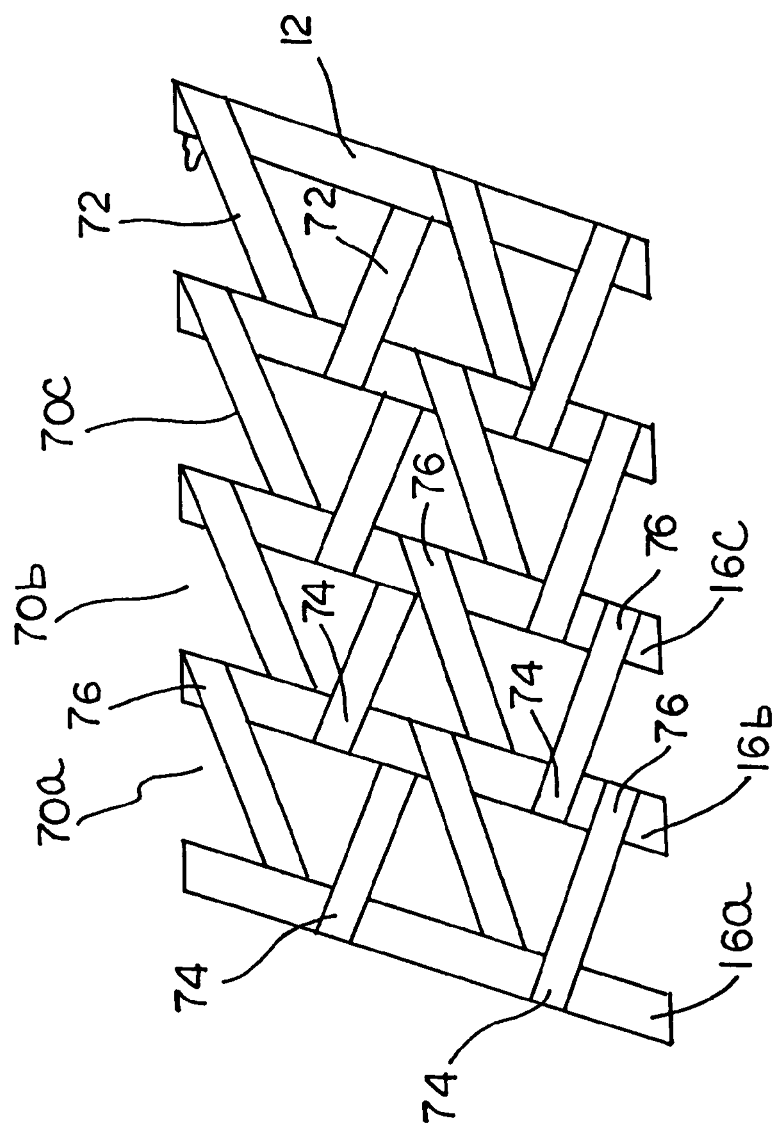
FIG. 19 is a side view of another embodiment of the spiral stent of FIG. 17 in an expanded position.

The first and second sections 74, 76 may engage and/or be attached to the loops 16 in several ways. For example, as seen in FIG. 17, the strip 72 may be looped around the loops 16, such that the strip 72 does not intersects itself between the first and second sections 74, 76 of the intermediate portions 70. Alternatively and/or additionally, as seen in FIG. 19, the strip 72 may cross through the loops 16, such that the strip 72 intersects itself between the first and second sections 74, 76 of the intermediate portions 70. The overlap of the spiral plane with the intermediate portions 70, may create a stronger stent 10 without reduce compressibility of the stent 10.

Figure 20:
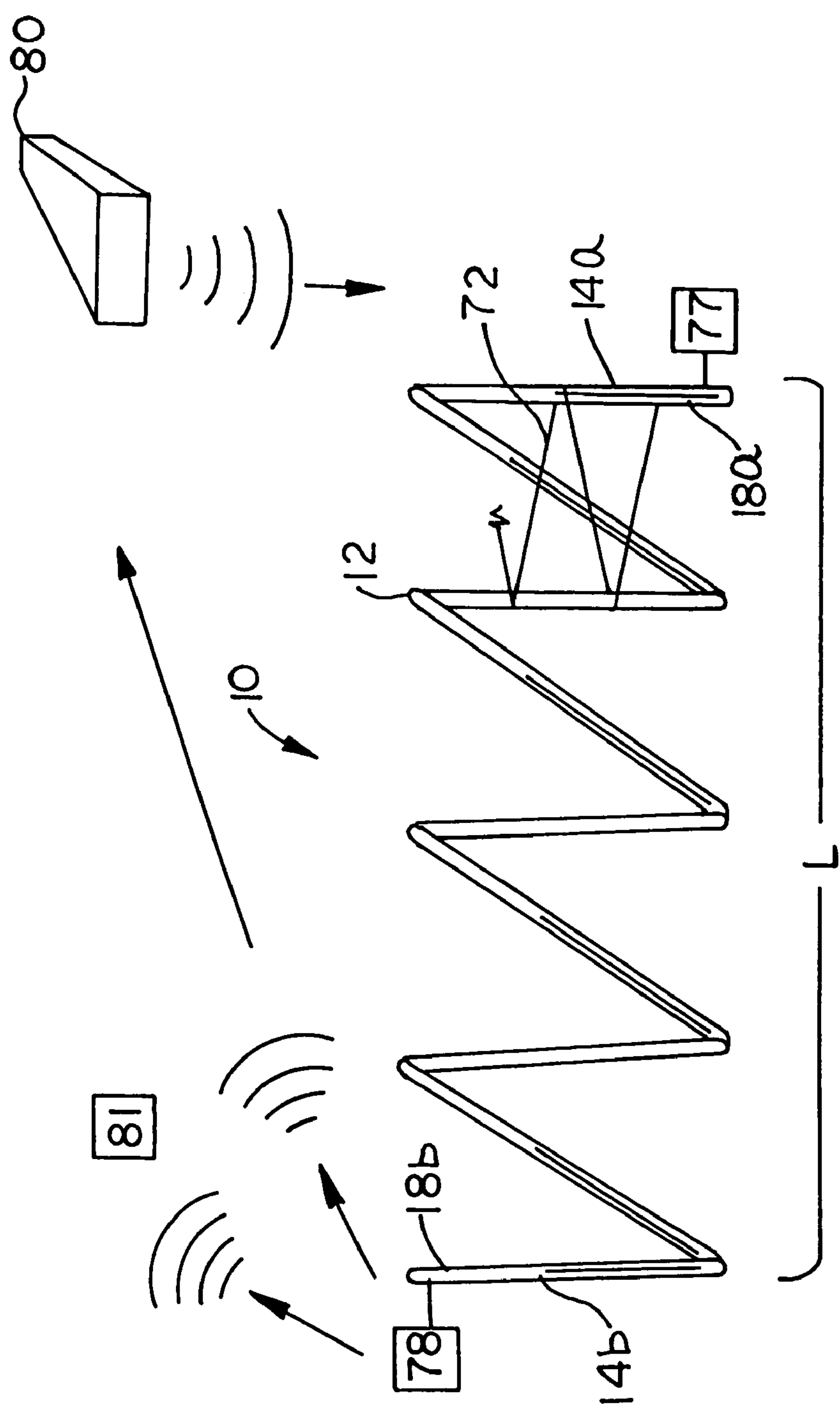
FIG. 20 is a block diagram of one embodiment of a medication dispending process, using the stent of FIG. 1.

In another exemplary embodiment, as seen in FIG. 20, the stent 10, with or without the intermediate sections 70, may further include one or more receivers 77 and/or one or more transmitters 78, or a combination thereof. The receivers 77 and/or transmitters 78 may be mounted and/or attached near the ends 14*a*, 14*b* and/or the free ends 18*a*, 18*b* of the stent 10, and may be activated and/or communicably coupled to the external power source 80. The external power source 80, in this exemplary embodiment, may send a pulse of power (electromagnetic wave or otherwise) to the receiver 77 along the length of the strip 12 and/or the strip 72 to the transmitter 78, which in turn may then send the signal back to the power source 80 or other suitable receiver 81 to confirm the continuity of the stent 10. The signal may also vary in strength if the strip 12 and/or the strip 72 was wearing. This variation in signal strength could give notice of impending failure.

The signal strength may be calibrated anytime during or after placement of the stent 10 in the vessel 40, and may be followed for the life of the stent 10. Additionally, this arrangement may be used as a tool to check the position of the graft 24, and/or to check for movement of the graft 24 without x-ray or other more invasive procedures. A suitable external source 80 that may provide power to the receivers 77 and/or transmitters 78 includes, but is not limited to, any type of machine able to emit electromagnetic waves, such as a radar gun, x-ray gun, etc. Calibrating at the time of placement may alleviate problems caused by varying tissue thicknesses in the patient and/or the blood vessel 40.

In one exemplary embodiment, the current and/or signal traveling through the electrical contacts 56, the receivers 77 and/or the transmitters 78 may be used to drive medication from the stent 10 into the surrounding tissue and/or to increase the penetration and effectiveness of the medications to the stent 10. More specifically, as is known in the art, the stent 10 may be coated with medication(s) prior to insertion of the stent 10 into the vessel 40. The current method of dissolving or removing the medication from the stent 10, includes letting the medication(s) be dissolved or removed from the stent 10 and into the surrounding tissue of the vessel 40, naturally. For example, the coating on the stent 10 may vary in thickness, destiny, and/or solubility, and as such may be controlled by the user. More specifically, the user may vary the above properties of the coating to accomplish the amount of medication(s) that is dissolved, for how long the medication(s) is dissolved, and/or how much per unit time of the medication(s) is dissolved.

Figure 21:
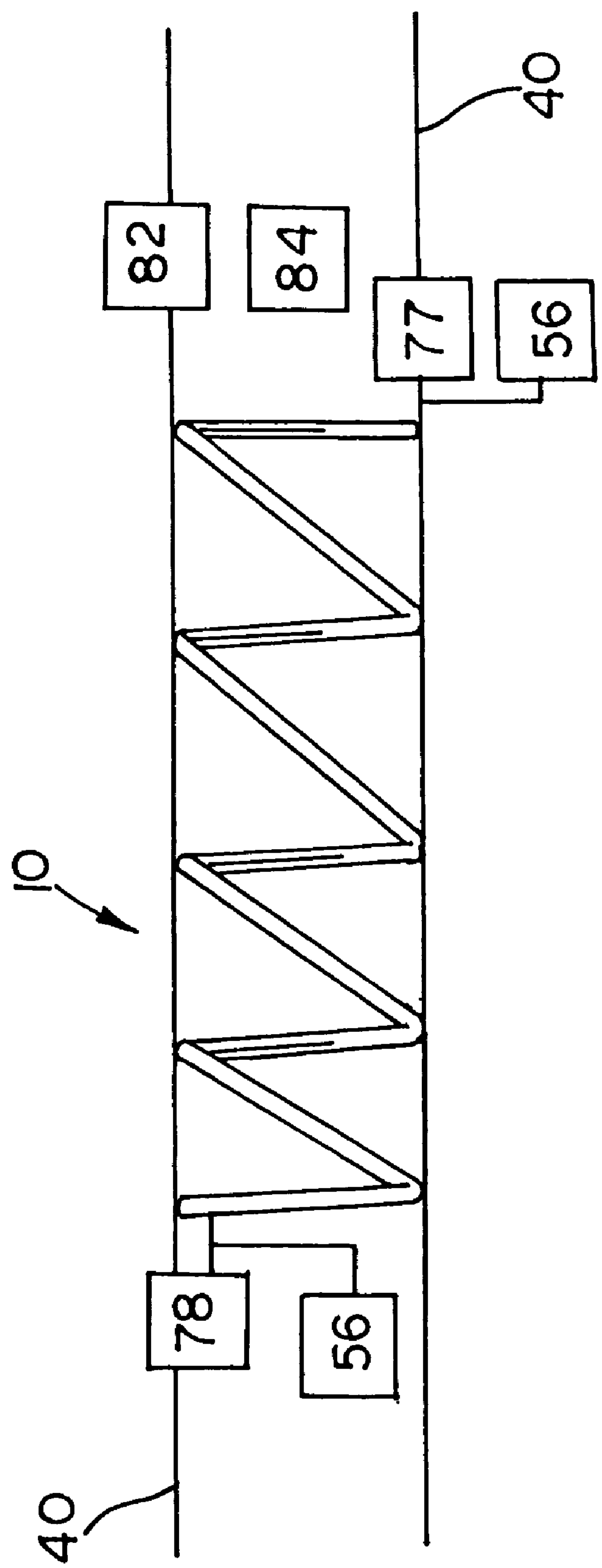
FIG. 21 is a block diagram of another embodiment of a medication dispending process, using the stent of FIG. 1.

The current and/or the signal traveling through the electrical contacts 56, the receivers 77 and/or the transmitters 78, however, may be used to dissolve the medication(s) in any manner desired by the user. More specifically, in addition to, or as an alternative to the natural dissolving of the medication(s), the user may use the current and/or the signal to activate the medication(s) coated on the stent 10. As such, the medication(s) may be released as needed or at timed intervals for maximum effectiveness. Additionally and/or alternatively, the electrical contacts 56, the receivers 77 and/or the transmitters 78, a microchip 82 may be used to control the release of medication(s) from the stent 10, as seen in FIG. 21.

In one exemplary embodiment, the micro chips 82 or other implantable mechanical, electrical, or electromechanical devices 84, may measure flow rates within the vessel 40 after insertion of the stent 10 in the patient. As such, the user may not only track and/or control the release of medication, but also track the flowrate through the vessel 40.

Figures 22, 23:
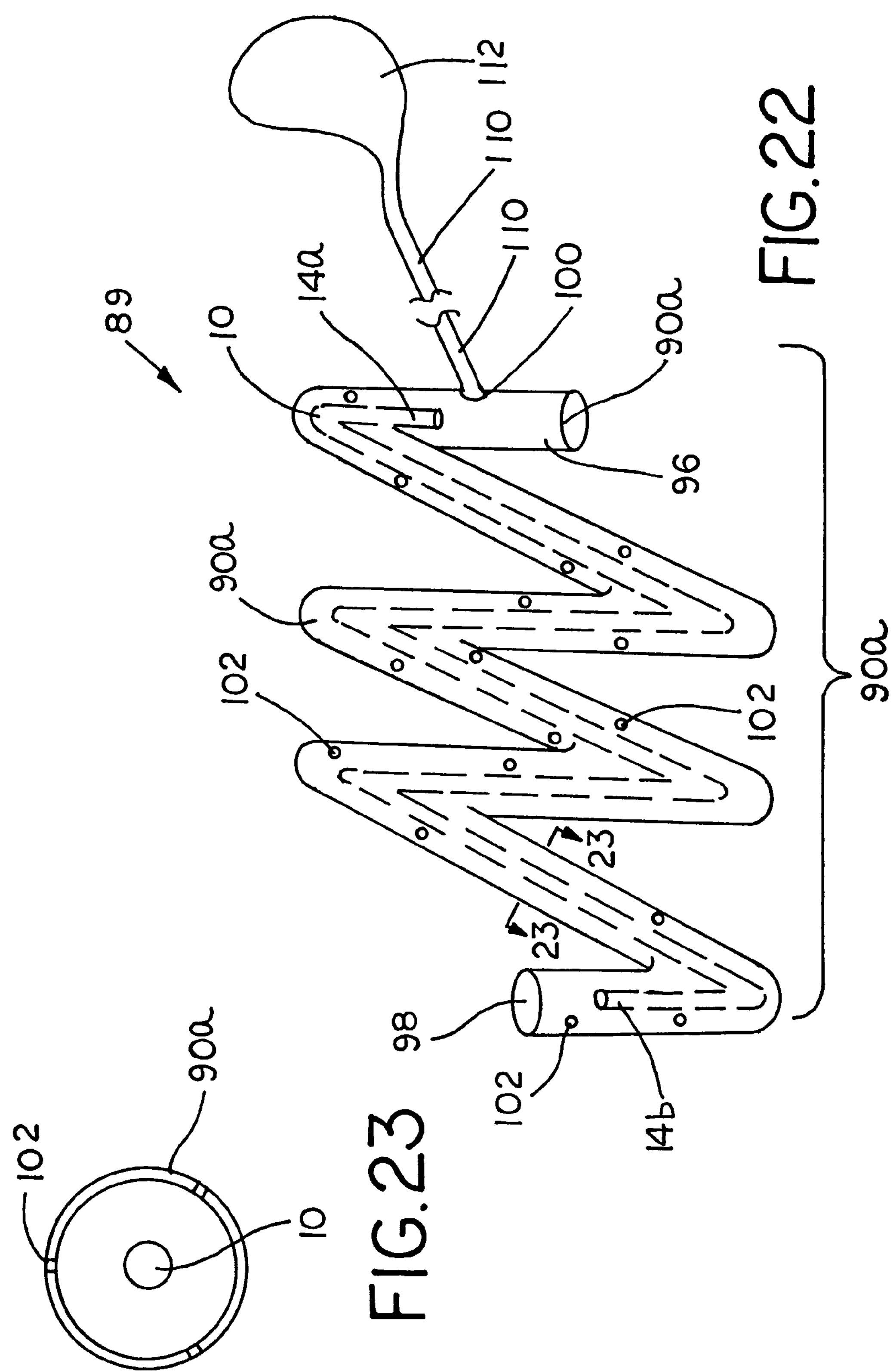
FIG. 22 is a side view of one exemplary embodiment of a fluid delivery system, using the stent of FIG. 1.
FIG. 23 is a sectional view of a soaker hose along lines 23-23 of FIG. 22.

As seen in FIG. 22, the stent 10, with or without the intermediate sections 70, may further include a fluid delivery system 89. The fluid delivery system 89, may include a fluid distribution member 90, a fluid connection member 110, and a reservoir 112. In one exemplary embodiment, as seen in FIGS. 22 and 23, the fluid distribution member 90 may be a generally elongate tube 90*a* having an inlet 100 and a plurality of outlets/apertures 102 for the receiving and distributing fluids, i.e. medication(s) including, but not limited to, anti-hyperplasia medications, antibiotics, and heparin to treat clots or improve flow. The elongate tube 90*a* may be flexible and may extend from the first end 14*a* to the second end 14*b* of the stent 10, and more specifically, may at least partially encompass the stent 10. For example, the stent 10 may be threaded through the elongate tube 90*a*, such that the elongate tube 90*a* acts as a sheath over stent 10 during use. The stent 10, for example, may be fully encapsulated by the elongate tube 90*a*, such that the stent 10 is disposed between a first end 96 and a second end 98 of the elongate tube 90*a*. The inlet 100 may be disposed anywhere along the elongate tube 90, and may be fluidly connected to the elongate tube 90*a*. The plurality of outlets/apertures 102, similarly, may be disposed anywhere along the elongate tube 90*a*, and may be disposed only in specific areas. For example, it may be desired to only release the fluid near first end 14*a* of the stent 10 and/or near the second end 14*b* of the stent 10, and as such, the apertures 102 may only be disposed on the elongate member 90*a* near the first and/or the second ends 14*a*, 14*b*.

Figure 24:
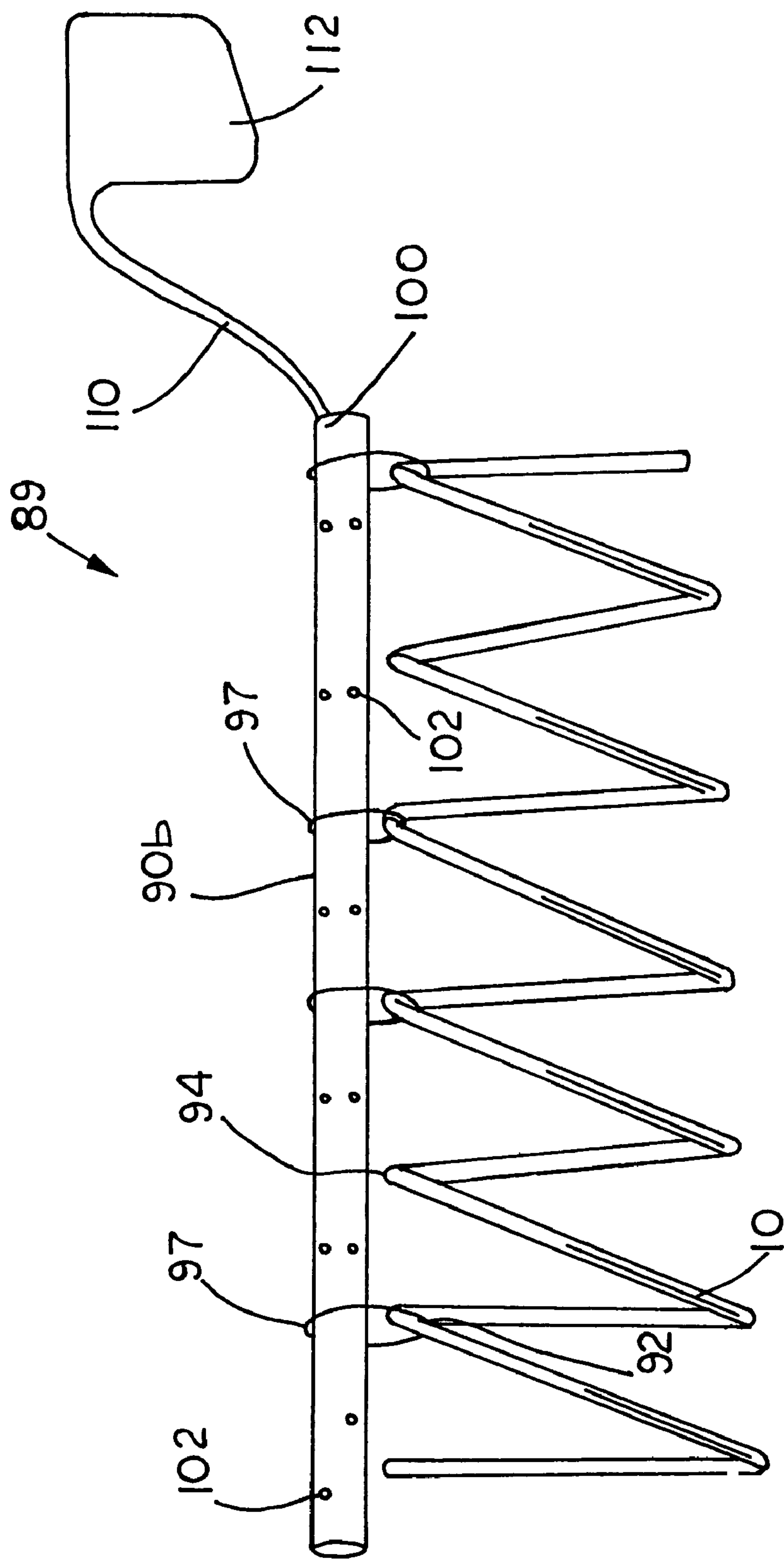
FIG. 24 is a side view of another exemplary embodiment of a fluid delivery system, using the stent of FIG. 1.

In another exemplary embodiment, as seen in FIG. 24, the fluid distribution member 90 may be a generally elongate tube 90*b* having an inlet 100 and a plurality of outlets/apertures 102. The elongate tube 90*b* may be rigid or flexible, and may be disposed on the stent 10. More specifically, the elongate tube 90*b* may be attached to an inner surface 92 of the stent and/or to an outer surface 94 the stent 10. The elongate tube 90*b* may be attached to the stent 10, in any number of ways, including but not limited to, stitching, gluing, melting, and/or fastening the elongate tube 90*b* to the stent 10 with one or more attaching members 97. The attaching member 97 may be any type of member adaptable to attach the elongate tube 90*b* to the stent 10, including but not limited to, thread, glue, etc.

Figure 25:
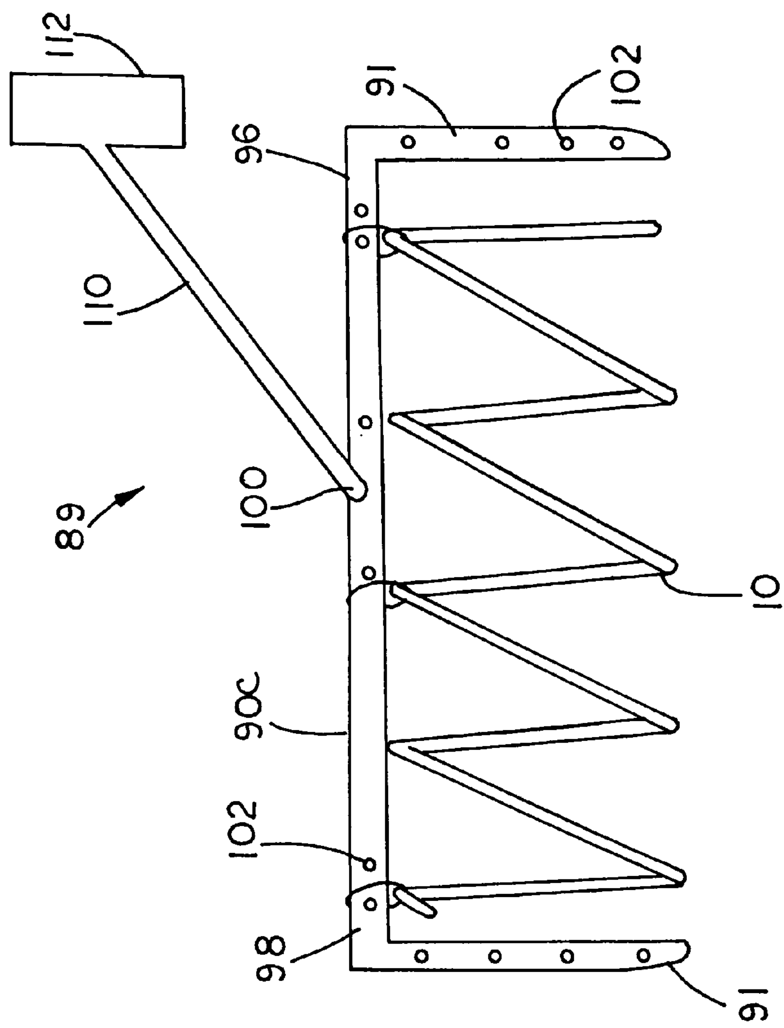
FIG. 25 is a side view of another exemplary embodiment of a fluid delivery system, using the stent of FIG. 1.
Figure 26:
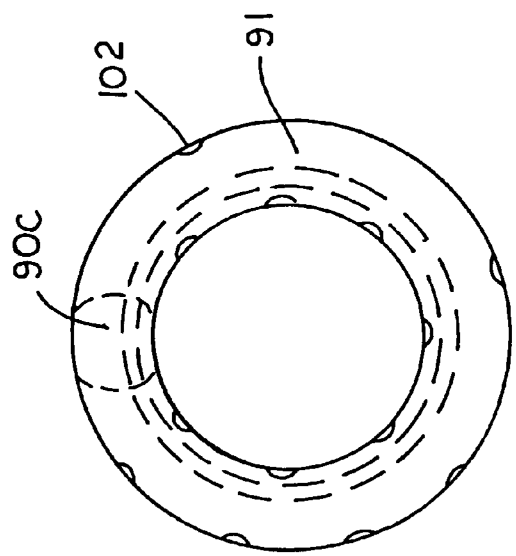
FIG. 26 is a front view of the fluid delivery system of FIG. 25.

In another exemplary embodiment, as seen in FIGS. 25 and 26, the fluid distribution member 90 may be a generally elongate tube 90*c* having one or more dependent members 91, such as the donut shaped tubes 91 disposed near the first end 96 and the second end 98 of the elongate tube 90*c*. The inlet 100 once again, may be disposed anywhere along the elongate tube 90*c*, and the plurality of outlets/apertures 102, may be disposed anywhere along the elongate tube 90*c* and/or the donut shaped tubes 91.

Figure 27:
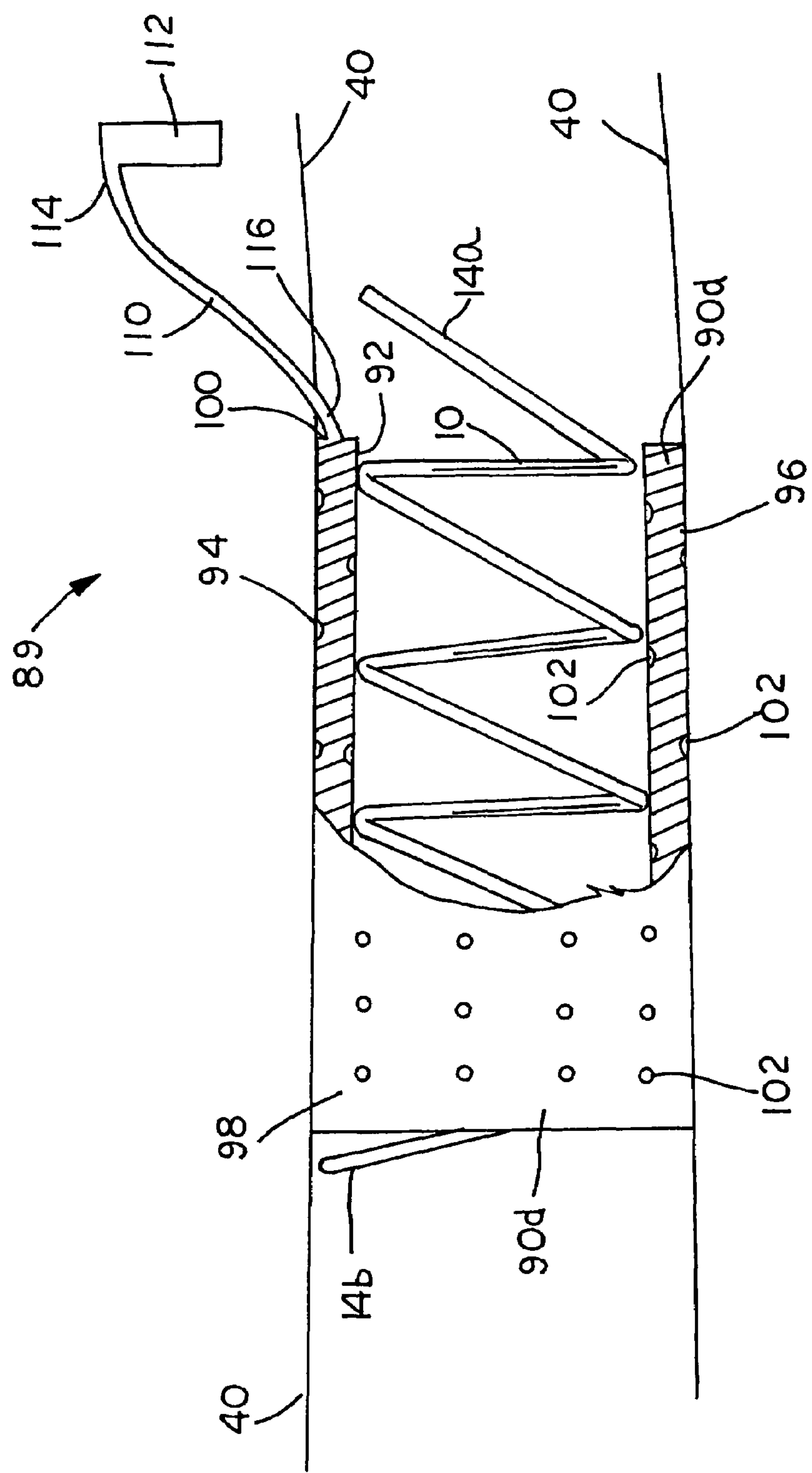
FIG. 27 is a side view of another exemplary embodiment of a fluid delivery system, using the stent of FIG. 1.
Figure 28:
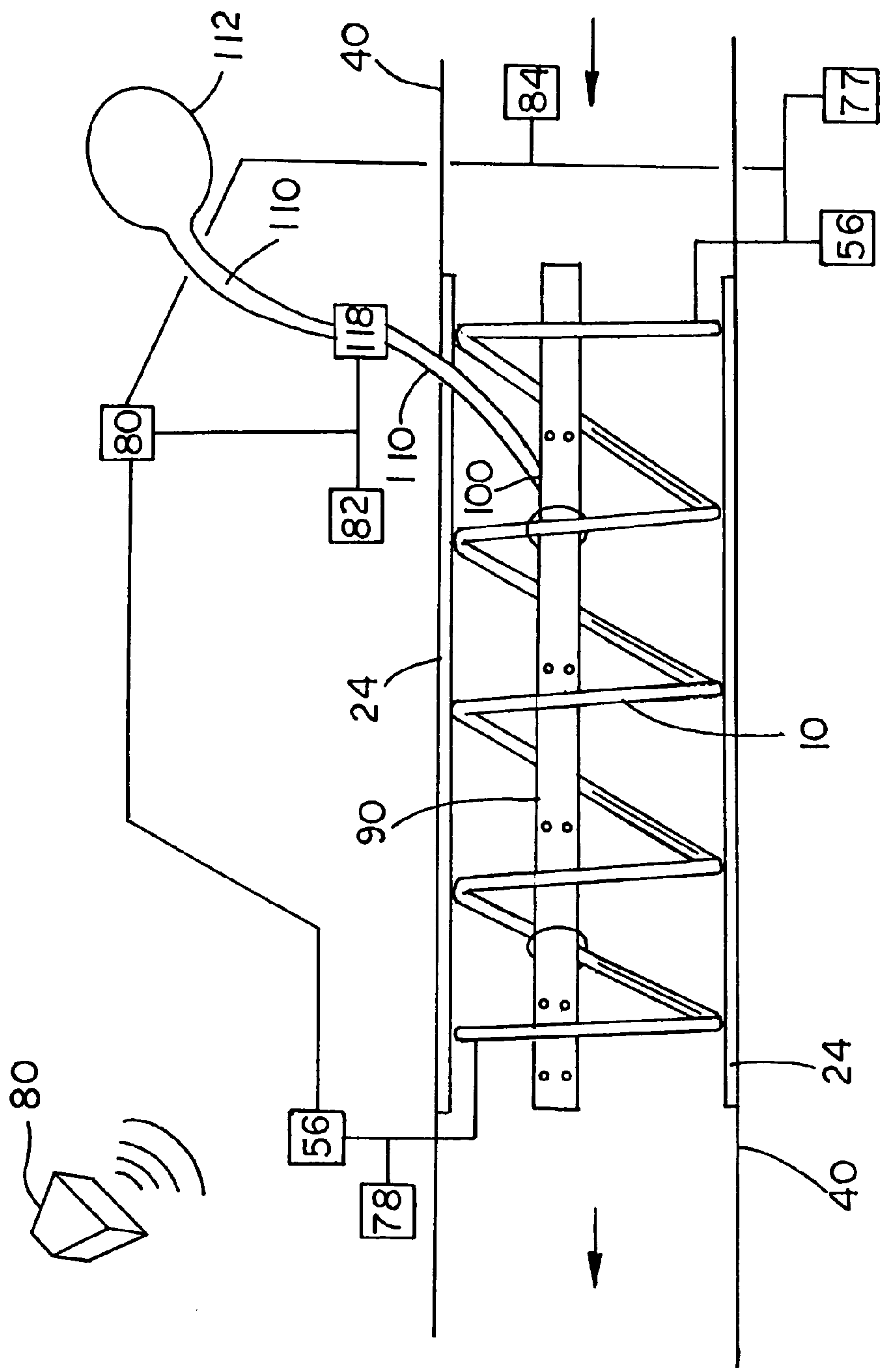
FIG. 28 is a side view of one exemplary embodiment of a smart graft, using the stent of FIG. 1.

In another exemplary embodiment, as seen in FIG. 27, a fluid distribution member 90*d* may include the inner surface 92, the outer surface 94, the first end 96, and the second end 98. The fluid distribution member 90*d* may have a generally tubular shape, and may be sized and shaped to correspond to the stent 10. More specifically, the first and second ends 96, 98 of the fluid distribution member 90*d* may be disposed between the first and second ends 14*a*, 14*b* of the stent 10, and the inner surface 92 of the fluid distribution member 90*d* may be disposed around, or adjacent to the stent 10. The fluid distribution member 90*d* may further include the one or more inlets 100, and the one or more outlets 102. The one or more inlets 100 may be located anywhere on the fluid distribution member 90*d*, and in this exemplary embodiment, may be fluidly connected near the first end 96, the second end 98, and/or the outer surface 94 of the fluid distribution member 90*d*. The one or more outlets 102 may also be located anywhere on the fluid distribution member 90*d*, and in this exemplary embodiment, may be disposed on the inner surface 92 and/or the outer surface 94. For example, for fluid intended to affect the area of the vessel 40 surrounding the fluid distribution member 90*d* and/or the graft 24, the one or more outlets 102 may be disposed on the outer surface 94 of the fluid distribution member 90*d*. Additionally and/or alternatively, for fluid intended to enter the flow of the vessel 40, the one or more outlets 102 may be disposed on the inner surface 92 of the fluid distribution member 90*d*.

The fluid connection member 110, such as a hose, tube, or the like, may fluidly connect the fluid distribution member 90 to the reservoir 112. The fluid connection member 110 includes an inlet 114 fluidly connected to the reservoir 112, and an outlet 116 fluidly connected to the inlet 100 of the fluid distribution member 90. It is contemplated, that additional fluid connection members 110 and/or additional reservoirs 112 may be used, such that, for example, one or more different fluids, may enter/exit at one or more inlets 100 and/or outlets 102 of the fluid distribution member 90.

The reservoir 112, as seen in FIGS. 22, 24, 25, and 27 may be fluidly connected to the fluid connection member 110 and/or the fluid distribution member 90, and may be adapted to receive, store, and/or eject the fluid toward the fluid distribution member 90. The reservoir 112 may be constructed in several ways and from many materials, and may incorporate different technologies. For example, the reservoir 112 may be a syringe adapted to inject fluid into the fluid connection member 110 and/or the fluid distribution member 90. The reservoir 112 may be a multiple stick expander type, metal backed reservoir 112, which could be palpated or located with a magnet, such that a variety of medications could be placed percutaneously to the graft site. The reservoir 112 may also be a flat reservoir 112 that may bubble on one side and a percutaneous delivery system lining up a male/female plug or insert could be built up radiographically to place any desired medication(s) in any concentration. External power source 80 could be used to open and close microchips to allow flow.

The above exemplary embodiments of the fluid deliver system 89 may include many variations thereof to achieve and/or create additional or alternative features. For example, the power source 80 may be used, in combination with a valve 118, and/or the microchip 82 to open or close the fluid connection to the fluid distribution member 90. As such, the graft 24, may be labeled a "smart" graft 24, that may monitor the integrity of the stent 10, monitor the flow through the vessel 40, and/or control the flow of the fluid from the fluid distribution member 90, such that, for example, specific medications may be delivered to the graft 24 to prolong and improve the useful life of the graft 24 and/or the stent 10. The various components of the fluid deliver system 89 may also be constructed from various materials, including but not limited to, GORE-TEX, DELRIN, SILICON, and/or any other type of material able to be safely used in a patient.

Numerous modifications and alternative embodiments will be apparent to those skilled in the art in view of the foregoing description. Accordingly, this description is to be construed as illustrative only. The details of the structure may be varied substantially without departing from the spirit and scope of the disclosure, and the exclusive use of all modifications which come within the scope of the eventual claims is reserved.

What is claimed is:

1. A stent assembly, comprising:

a spiral shaped elongate member having a first end and a second end, wherein the elongate member includes a plurality of spiraling loops extending between the first end and the second end, the loops being spaceable so as not to touch each other;

a first contact attached adjacent the first end of the elongate member;

a second contact attached adjacent the second end of the elongate member, wherein the first and second contacts are coupled to a power generator, the power generator arranged to allow a current to be passed from the first contact to the second contact, and a measuring device that measures current or voltage passing between the first and second contacts.

2. The stent assembly of claim 1, wherein the elongate member is constructed from one contiguous strip.

3. The stent assembly of claim 1, wherein the loops each have a rectangular cross-section.

4. The stent assembly of claim 1, wherein the measuring device is a voltmeter.

5. The stent assembly of claim 1, wherein the measuring device measures current.

6. The stent assembly of claim 1, wherein the measuring device measures voltage.

7. The stent assembly of claim 1, wherein measured information is communicated to an external communications device from an internal communications device.

8. A stent assembly comprising:

a spiral shaped elongate member having a first end and a second end, wherein the elongate member includes a plurality of spiraling loops extending between the first end and the second end, the loops being spaceable so as not to touch each other;

a first contact attached adjacent the first end of the elongate member; and a second contact attached adjacent the second end of the elongate member, wherein the first and second contacts are coupled to power generator, the power generator arranged to allow a current to be passed from the first contact to the second contact, wherein a height of the plurality of loops measured along a radial axis of the plurality of loops is greater than a width of the plurality of loops measured along a longitudinal axis of the plurality of loops.

9. The stent assembly of claim 1, wherein the power generator is an internal power source.

10. The stent assembly of claim 9, wherein the internal power source is a subcutaneous pack.

11. The stent assembly of claim 9, wherein the internal power source is a battery.

12. A stent assembly, comprising:

a spiral shaped elongate member having a first end and a second end, wherein the elongate member includes a plurality of spiraling loops extending between the first end and the second end, the loops being spaceable so as not to touch each other;

a first contact attached adjacent the first end of the elongate member;

a second contact attached adjacent the second end of the elongate member, wherein the first and second contacts are coupled to a power source, the power source arranged to allow a current to be passed from the first contact to the second contact, and a measuring device that measures current or voltage passing between the first and second contacts.

* * * * *